(12) United States Patent
Razeto et al.

(10) Patent No.: US 10,504,252 B2
(45) Date of Patent: Dec. 10, 2019

(54) METHOD OF, AND APPARATUS FOR, REGISTRATION AND SEGMENTATION OF MEDICAL IMAGING DATA

(71) Applicant: Toshiba Medical Systems Corporation, Otawara-shi (JP)

(72) Inventors: Marco Razeto, Edinburgh (GB); Akinola Akinyemi, Edinburgh (GB); Chris McGough, Edinburgh (GB); Tyler Stroud, Edinburgh (GB)

(73) Assignee: Canon Medical Systems Corporation, Otawara-shi (JP)

( * ) Notice: Subject to any disclaimer, the term of this patent is extended or adjusted under 35 U.S.C. 154(b) by 61 days.

(21) Appl. No.: 14/569,890

(22) Filed: Dec. 15, 2014

(65) Prior Publication Data

US 2016/0171698 A1 Jun. 16, 2016

(51) Int. Cl.
*G06T 3/00* (2006.01)
*G06T 7/33* (2017.01)
(Continued)

(52) U.S. Cl.
CPC ............ *G06T 11/20* (2013.01); *G06T 3/0068* (2013.01); *G06T 7/12* (2017.01); *G06T 7/149* (2017.01);
(Continued)

(58) Field of Classification Search
CPC ..... A61B 5/0555; A61B 6/027; A61B 6/5211; A61B 6/5217; A61B 6/5223;
(Continued)

(56) References Cited

U.S. PATENT DOCUMENTS 7,058,210 B2   6/2006  Mundy et al.
7,292,714 B2  11/2007  Seissler et al.
(Continued)

FOREIGN PATENT DOCUMENTS

JP   2003-225231   8/2003
JP   2004-508118   3/2004
(Continued)

OTHER PUBLICATIONS

Jeroen G. Snel et al. "Quantitative in vivo analysis of the kinematics of carpal bones from three-dimensional CT images using a deformable surface model and a three-dimensional matching technique", Med.Phys. 27, 2000, 12 pages.
(Continued)

*Primary Examiner* — Chante E Harrison
(74) *Attorney, Agent, or Firm* — Oblon, McClelland, Maier & Neustadt, L.L.P.

(57) ABSTRACT

An imaging data processing apparatus comprises a registration unit configured to obtain a hierarchical registration between a reference data set and volumetric medical imaging data, the reference data set comprising a plurality of anatomical structures, wherein the hierarchical registration comprises an initial registration and at least one further registration, and the at least one further registration is obtained by the registration unit by modifying the initial registration, and a segmentation unit for segmenting at least part of the volumetric medical imaging data in dependence on the hierarchical registration. The initial registration comprises a registration between at least part of the reference data set and at least part of the volumetric medical imaging data, the at least part of the reference data set comprising a first anatomical structure or first group of anatomical structures. The at least one further registration comprises a registration between a subset of the reference data set and at
(Continued)

least part of the volumetric medical imaging data, the subset of the reference data set comprising a second, different anatomical structure or second, different group of anatomical structures.

22 Claims, 11 Drawing Sheets

(51) Int. Cl.
    *G06T 7/12*           (2017.01)
    *G06T 7/149*         (2017.01)
    *A61B 6/03*           (2006.01)
    *A61B 6/00*           (2006.01)
    *G06T 11/20*         (2006.01)

(52) U.S. Cl.
    CPC .............. *G06T 7/33* (2017.01); *A61B 6/032* (2013.01); *A61B 6/037* (2013.01); *A61B 6/4085* (2013.01); *G06T 2207/10072* (2013.01); *G06T 2207/20016* (2013.01); *G06T 2207/20128* (2013.01); *G06T 2207/30008* (2013.01)

(58) Field of Classification Search
    CPC ... A61B 6/5229; A61B 6/5247; A61B 6/5288; A61B 8/5292; A61B 5/1113; G06T 2207/30004; G06T 7/30; G06T 7/11; G06T 7/149; G06T 15/08; G06T 19/20; G06T 2207/20016; G06T 2207/20128; G06T 2207/20108; G06K 2209/05
    USPC .................. 345/424, 419; 382/131, 128, 132
    See application file for complete search history.

(56) References Cited

U.S. PATENT DOCUMENTS

| | | | |
|---|---|---|---|
| 7,567,696 B2 | 7/2009 | Moreau-Gobard et al. | |
| 7,623,731 B2 * | 11/2009 | Lim | G06T 7/20 382/277 |
| 7,916,919 B2 | 3/2011 | Zheng et al. | |
| 7,991,210 B2 | 8/2011 | Peterson et al. | |
| 8,068,652 B2 | 11/2011 | Avinash et al. | |
| 8,577,115 B2 | 11/2013 | Gering et al. | |
| 2005/0004443 A1 | 1/2005 | Okerlund et al. | |
| 2007/0206880 A1 * | 9/2007 | Chen | G06K 9/00 382/294 |
| 2010/0054630 A1 * | 3/2010 | Avinash | G06F 3/04845 382/294 |
| 2011/0052033 A1 * | 3/2011 | Shekhar | A61B 6/037 382/131 |
| 2011/0317898 A1 * | 12/2011 | Shi | G06T 7/0024 382/131 |
| 2013/0094749 A1 * | 4/2013 | Oh | A61B 6/503 382/133 |
| 2015/0023575 A1 * | 1/2015 | Valadez | G06T 7/0081 382/131 |
| 2015/0131882 A1 * | 5/2015 | Mohr | G06T 7/0081 382/131 |
| 2015/0161786 A1 * | 6/2015 | Seifert | G06T 7/0012 382/119 |
| 2015/0363937 A1 * | 12/2015 | Weistrand | G06T 7/0089 382/131 |

FOREIGN PATENT DOCUMENTS

| | | |
|---|---|---|
| JP | 2005-169118 | 6/2005 |
| JP | 2007-244887 | 9/2007 |
| JP | 2010-055615 | 3/2010 |
| JP | 2011-512999 | 4/2011 |
| JP | 2012-30072 | 2/2012 |
| WO | WO 2012/103949 A1 | 8/2012 |

OTHER PUBLICATIONS

Hyunjin Park et al. "Construction of an Abdominal Probabilistic Atlas and its Application in Segmentation", IEEE Transactions on Medical Imaging, vol. 22, No. 4, 2003, 10 pages.

X. Zhuang et al. "Robust registration between cardiac MRI images and atlas for segmentation propagation", SPIE vol. 6914 Medical Imaging 2008: Image Processing, 6914, 07, 2008, 11 pages.

O. Ecabert et al. "Automatic heart segmentation in CT: current and future applications", Clinical Applications, MedicaMundi 50/3, 2006, 6 pages.

Martin Koch et al. "Fully Automatic Segmentation of Wrist Bones for Arthritis Patients", IEEE Symposium on Biomedical Imaging, 2011, 5 pages.

Hisao Moritomo et al. "In Vivo Three-Dimensional Kinematics of the Midcarpal Joint of the Wrist", The Journal of Bone and Joint Surgery, 2006, 11 pages.

Maria Murgasova et al. "Robust Segmentation of Brain Structures in MRI", Biomedical Imaging: From Nano to Macro, 2009, 4 pages.

Japanese Office Action dated Sep. 3, 2019 in Japanese Application No. 2015-243855, 4 pages.

\* cited by examiner

METHOD OF, AND APPARATUS FOR, REGISTRATION AND SEGMENTATION OF MEDICAL IMAGING DATA

FIELD

Embodiments described herein relate generally to a method of, and apparatus for, registration and segmentation of medical imaging data. Embodiments have, for example, application to automatic registration and segmentation of bones or other tissues belonging to anatomical joints.

BACKGROUND

A variety of medical imaging modalities, for example computerized tomography (CT), magnetic resonance imaging (MRI) and positron emission tomography (PET), have become standard techniques in obtaining medical imaging data representative of a patient or other subject for diagnostic or other purposes. Medical imaging data can be in a variety of forms and can for example include any suitable data obtained from measurements by a medical imaging modality and/or any suitable data representative of one or more anatomical features. Medical imaging data may be any data that can be rendered, or otherwise processed, to obtain an image of at least part of a patient or other medical subject and/or any data that can be rendered, or otherwise processed, to obtain an image of one or more anatomical features. Volumetric medical imaging data may, for example, be in the form of an array of voxels. Such arrays of voxels may for example be representative of intensity, absorption or other parameter as a function of three-dimensional position, and may for example be obtained by suitable processing of measurement signals obtained by a medical imaging modality.

The wrist is one of the most intricate articulations of the musculoskeletal system. The wrist comprises eight small bones (the carpal bones) and a complex intrinsic and extrinsic ligament system, which is illustrated in FIG. 1. FIG. 2 shows the eight small carpal bones 10A to 10H together with parts of the radius 12 and ulna 14 (the bones of the forearm). FIG. 2 also shows parts of the metacarpal bones 16.

Because of the complexity of the wrist, injuries to the bones or ligaments of the wrist may potentially cause irreversible disruption to the movement of the wrist, and may initiate progressive osteoarthritis.

It is known to study the movement of the wrist by taking a series of images of the wrist, each image being taken with the wrist at a different position. For example, the wrist may be moved such that the hand moves from side to side in the plane of the hand, as in a waving motion (this motion may be referred to as radial-ulnar deviation). The movement of the wrist may be studied to provide a comparison of the movement pre- and post-treatment, for example to determine a change in movement due to surgery.

In certain contexts, a neutral phase of a wrist movement may be taken as being the midpoint between the two extremes of motion (or may be taken as being in some other position in other contexts). Textbook drawings and other anatomical drawings of the wrist may in general be presented in neutral phase. For example, FIGS. 1, 2, and 3 show a wrist presented in neutral phase.

Presentation of data using techniques typical of illustrative anatomical drawings (for example, presentation of the bones of a joint in an exploded or disarticulated view) can provide further information about a joint and shed further light on pathologies. An example of such a presentation is shown in FIG. 4. Preparing such visualizations can be a time-consuming and labor-intensive task.

The analysis of the kinematics of the wrist joint and the analysis of individual bones in the wrist may be difficult and time-consuming. Bones of interest may be required to be identified manually. The neutral phase may be required to be identified in a series of images taken at different phases of motion. Pathology may need to be identified. Pre- and post-treatment images may be compared. The analysis may be made more complicated by the presence of malformations.

Appropriate presentation and visualization of patient volumetric data can improve reading time and improve diagnosis.

FIG. 5 shows a scan image of a patient's wrist. It may in some circumstances be difficult for a clinician to obtain all the information that he or she may desire from a scan image such as that of FIG. 5. In some circumstances, pathology, trauma and scanning condition can hinder clear visualization of patient anatomy.

It is known to create atlases of the human anatomy, or atlases of particular parts of the human anatomy. Known atlases comprise a set of voxels, each voxel comprising image intensity and position data, and may further comprise position data indicating the position of particular anatomical features in the atlas. It has also been suggested to include other statistical measures relating to intensity in an atlas.

Atlases may be used in the processing or analysis of imaging data obtained by measurements on a patient. It is known to register imaging data to atlas data using rigid, affine or non-rigid registration, thereby obtaining a rigid, affine or non-rigid transformation which may be applied to the imaging data to align anatomical features in the imaging data with corresponding anatomical features in the atlas. A rigid registration may comprise translation and/or rotation. An affine registration may comprise translation, rotation, scaling and/or shearing.

Techniques for registration of images are well-known. In general, registration is an optimization problem, with the aim of finding an optimal transformation between two sets of imaging data. The transformation relates corresponding features in the sets of imaging data by mapping points in the coordinate system of one set of imaging data onto the corresponding points in the coordinate system of the other set of imaging data. The optimal transformation may be determined by maximizing (or minimizing) a similarity measure, for example mutual information.

The use of such atlases and registration procedures may enable, for example, direct comparisons to be performed between imaging data obtained from different subjects.

Segmentation is the process of identifying pixels or voxels representing a given structure in an image, which may include separating the pixels or voxels from the rest of the image. The structure may be, for example, an anatomical structure such as a bone, a vessel or an organ. The identification and/or separation of pixels or voxels representing the structure may facilitate further processing of information relating to the structure, for example, measurement of the structure, or rendering the structure in a way that is distinct from other structures in the image.

BRIEF DESCRIPTION OF THE DRAWINGS

Embodiments are now described, by way of non-limiting example, and are illustrated in the following figures, in which.

Each of FIGS. 1, 2 and 3 is a schematic illustration of the wrist.

DETAILED DESCRIPTION

Certain embodiments provide an imaging data processing apparatus comprising a registration unit configured to obtain a hierarchical registration between a reference data set and volumetric medical imaging data, the reference data set comprising a plurality of anatomical structures, wherein the hierarchical registration comprises an initial registration and at least one further registration, and the at least one further registration is obtained by the registration unit by modifying the initial registration, and a segmentation unit for segmenting at least part of the volumetric medical imaging data in dependence on the hierarchical registration. The initial registration comprises a registration between at least part of the reference data set and at least part of the volumetric medical imaging data, the at least part of the reference data set comprising a first anatomical structure or first group of anatomical structures. The at least one further registration comprises a registration between a subset of the reference data set and at least part of the volumetric medical imaging data, the subset of the reference data set comprising a second, different anatomical structure or second, different group of anatomical structures.

Certain embodiments provide an imaging data processing method comprising obtaining a hierarchical registration between a reference data set and volumetric medical imaging data, the reference data set comprising a plurality of anatomical structures, wherein the hierarchical registration comprises an initial registration and at least one further registration obtained by modifying the initial registration; and segmenting at least part of the volumetric imaging data in dependence on the hierarchical registration; wherein the initial registration comprises a registration between at least part of the reference data set and at least part of the volumetric medical imaging data, the at least part of the reference data set comprising a first anatomical structure or first group of anatomical structures; and wherein the at least one further registration comprises a registration between a subset of the reference data set and at least part of the volumetric medical imaging data, the subset of the reference dataset comprising a second, different anatomical structure or second, different group of anatomical structures.

Figure 1:
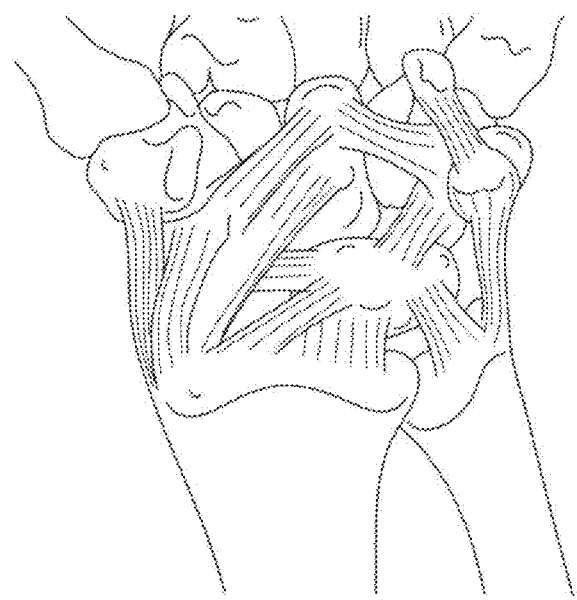
Figure 2:
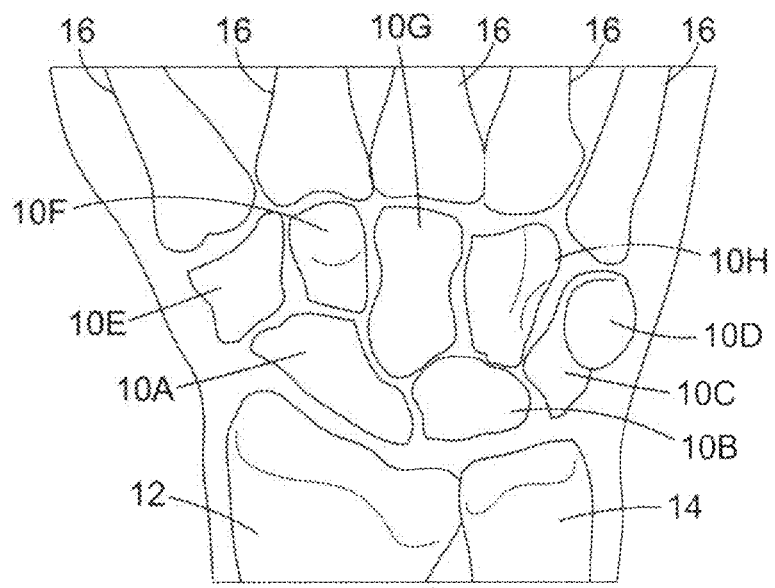
Figure 3:
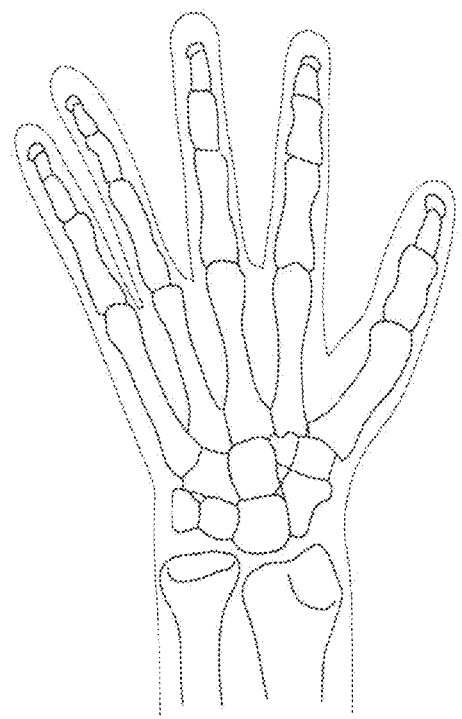
Figure 4:
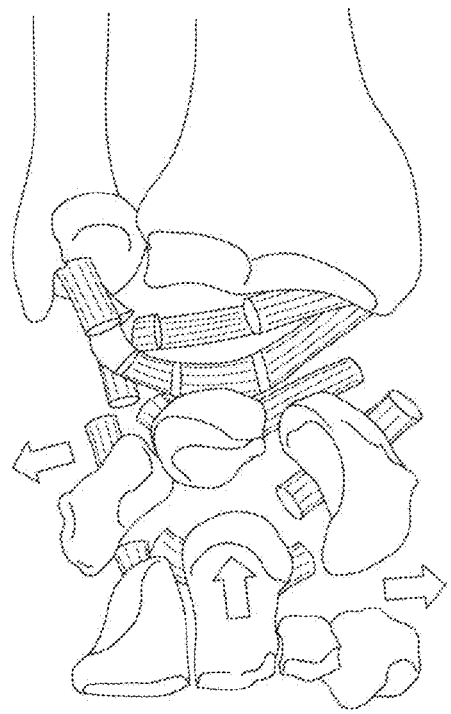
FIG. 4 is a schematic illustration of the wrist prepared in the form of an illustrative anatomical drawing.
Figure 5:
FIG. 5 is a scan image of the wrist.
Figure 6:
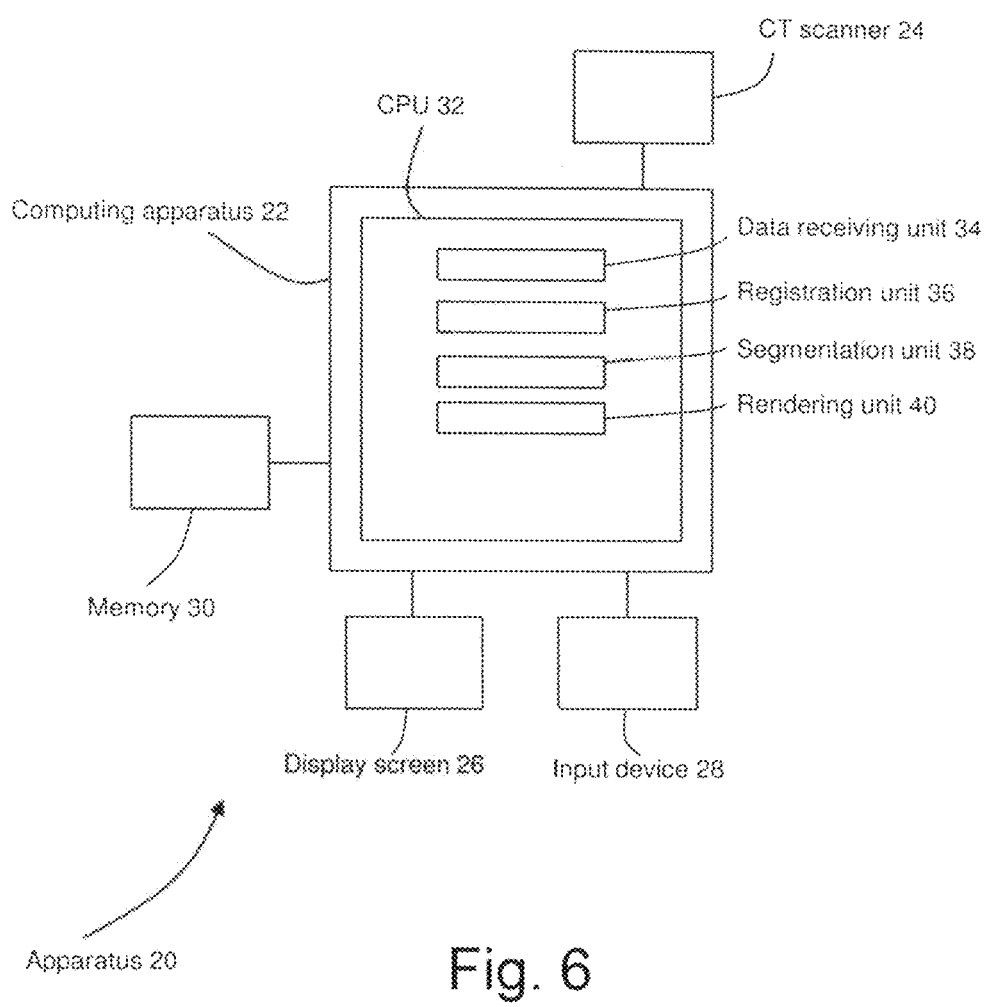
FIG. 6 is a schematic illustration of an apparatus according to an embodiment.

An imaging data processing apparatus 20 according to an embodiment is illustrated schematically in FIG. 6. The imaging data processing apparatus 20 comprises a computing apparatus 22, in this case a personal computer (PC) or workstation, which is connected to a CT scanner 24, one or more display screens 26 and an input device or devices 28, such as a computer keyboard, mouse or trackball.

The CT scanner 24 may be any CT scanner that is configured to obtain volumetric imaging data of a region of a patient. In the present embodiment, the region of the patient is a wrist. In other embodiments, the region of the patient may be any appropriate region, for example any joint such as a wrist, ankle, knee, elbow or neck. The volumetric imaging data may comprise multiple image data sets, each of which corresponds to a scan of the wrist in a different position.

In alternative embodiments, the CT scanner 24 may be replaced or supplemented by a scanner in any other imaging modality, for example an MRI (magnetic resonance imaging) scanner, X-ray scanner, PET scanner (positron emission tomography), SPECT (single photon emission computed tomography) scanner, Cone Beam CT scanner, or C-Arm X-ray scanner able to perform rotational X-ray.

In the present embodiment, image data sets obtained by the CT scanner 24 are stored in memory 30 and subsequently provided to computing apparatus 22. In an alternative embodiment, image data sets are supplied from a remote data store (not shown) which may form part of a Picture Archiving and Communication System (PACS). The memory 30 or remote data store may comprise any suitable form of memory storage.

Computing apparatus 22 provides a processing resource for automatically or semi-automatically processing image data sets, and comprises a central processing unit (CPU) 32.

The computing apparatus 22 includes a data receiving unit 34 for receiving volumetric imaging data, a registration unit 36 for registering such volumetric imaging data to an atlas, and a segmentation unit 38 for segmenting structures in the volumetric imaging data. In the present embodiment, the computing apparatus 22 further comprises a rendering unit 40 for rendering an image of the segmented data.

In the present embodiment, the data receiving unit 34, registration unit 36, segmentation unit 38 and rendering unit 40 are each implemented in computing apparatus 22 by means of a computer program having computer-readable instructions that are executable to perform the method of the embodiment. However, in other embodiments, the various units may be implemented as one or more ASICs (application specific integrated circuits) or FPGAs (field programmable gate arrays).

The computing apparatus 22 also includes a hard drive and other components of a PC including RAM, ROM, a data bus, an operating system including various device drivers, and hardware devices including a graphics card. Such components are not shown in FIG. 6 for clarity.

The system of FIG. 6 is configured to perform the method of embodiments that are described below with reference to FIGS. 7, 10, 11 and 14.

Figure 7:
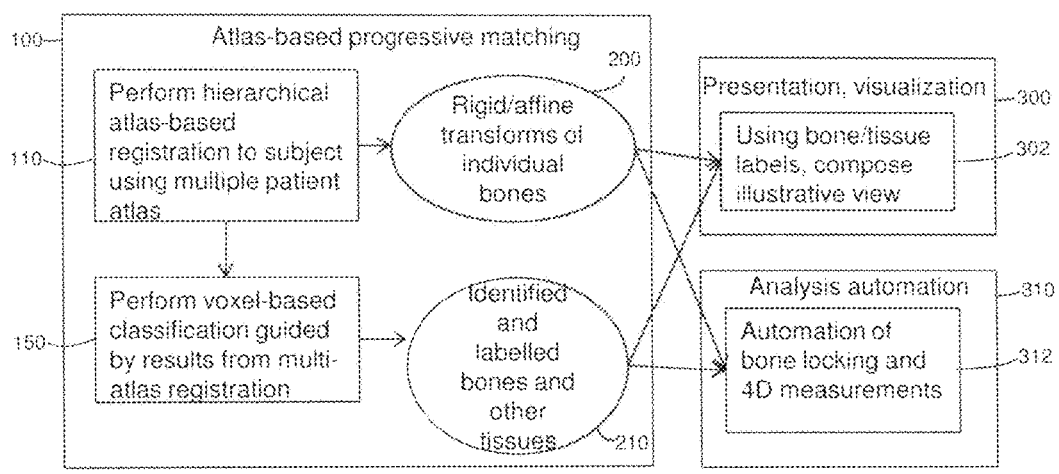
FIG. 7 is a flow chart illustrating in overview a process performed in accordance with an embodiment.

FIG. 7 is a flow chart illustrating in overview a method of an embodiment. The method comprises an atlas-based progressive matching 100 of multiple imaging data sets 70 using a multiple patient atlas (atlas data set 60).

Atlas-based matching may be used, for example, to indicate the process of applying an atlas to a data set for the purpose of segmenting the data set. Atlas-based progressive matching may be, for example, a process in which various components of the atlas are progressively aligned in different registrations, as described below.

The multiple imaging data sets 70 are derived from successive CT scans of the wrist of a patient. The successive CT scans are taken as the wrist of the patient is moved through a range of motion (in the present embodiment, radial-ulnar deviation).

The atlas-based progressive matching 100 comprises a hierarchical atlas-based registration 110 between the atlas data set 60 and at least one of the imaging data sets 70. The hierarchical atlas-based registration 110 may be performed in accordance with a method as described in detail below with reference to FIGS. 10 and 11, or by any suitable method. The hierarchical atlas-based registration 110 results in a set of rigid or affine transformations 200. Each of the rigid or affine transformations 200 relates a respective individual bone in the imaging data set 70 to the representation of that bone in the atlas data set 60. Each transformation 200 is the transformation that is required to transform the representation of a given one of the bones in the atlas data set 60 into the coordinate space of the volumetric data set, or vice versa. The hierarchical atlas-based registration 110 may be described as a piecewise registration, since different registrations may be performed for different individual bones.

The atlas-based progressive matching 100 further comprises a voxel-based classification of at least one of the imaging data sets 70, which is performed in dependence on the results of the hierarchical atlas-based registration 110. The voxel-based classification 150 may be guided by the results from the hierarchical atlas-based registration 150. The voxel-based classification 150 results in a set of identified and labeled bones and other tissues 210 in the at least one imaging data set 70. The voxel-based classification 150 may be performed in accordance with a method detailed below with reference to FIG. 10, or by any suitable method.

The rigid transformations 200 and identification and labeling data 210 are used for presentation and visualization 300 of the or each imaging data set 70. Using bone and tissue labels, an illustrative view of the patient's wrist may be rendered in 302. Such rendering is discussed in detail below with reference to FIG. 10. The rigid or affine transformations 200 and identification and labeling data 210 are further used to perform automated analysis 310 of the motion of the wrist. The automated analysis 310 comprises automation of bone locking and 4D measurements 312. Such automated analysis is discussed in detail below with reference to FIG. 14.

Figure 8:
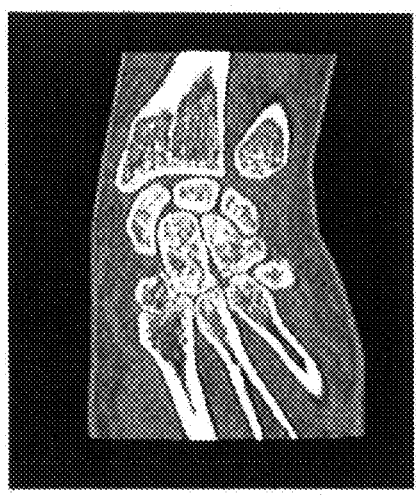
FIG. 8 is a pre-segmentation image of the wrist.
Figure 9:
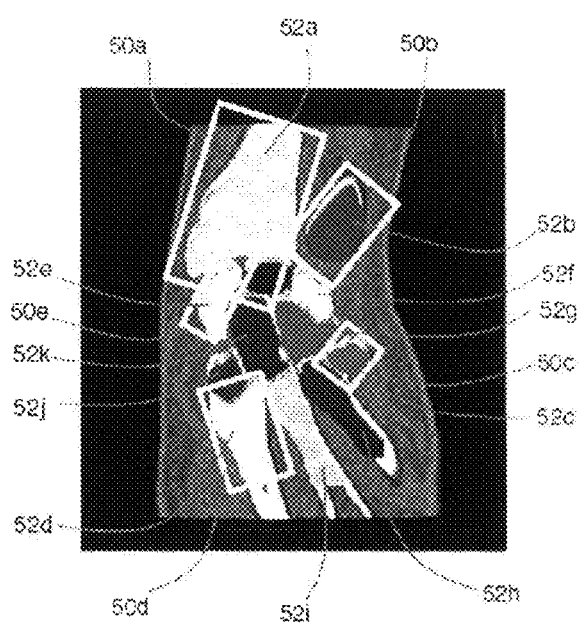
FIG. 9 shows the image of FIG. 8 overlaid with segmentation information.

FIG. 8 shows an image that has been rendered from volumetric imaging data. The image is representative of the wrist. FIG. 9 shows the same image after the process of FIG. 6 has been performed, resulting in identified and labeled structures (wrist bones) in the image, which are indicated by boxes 50a to 50e and/or regions 52a to 52k. The boxes and regions are representative of segmentation information (labels and regions indicative of a segmentation of at least part of the volumetric imaging data).

Figure 10:
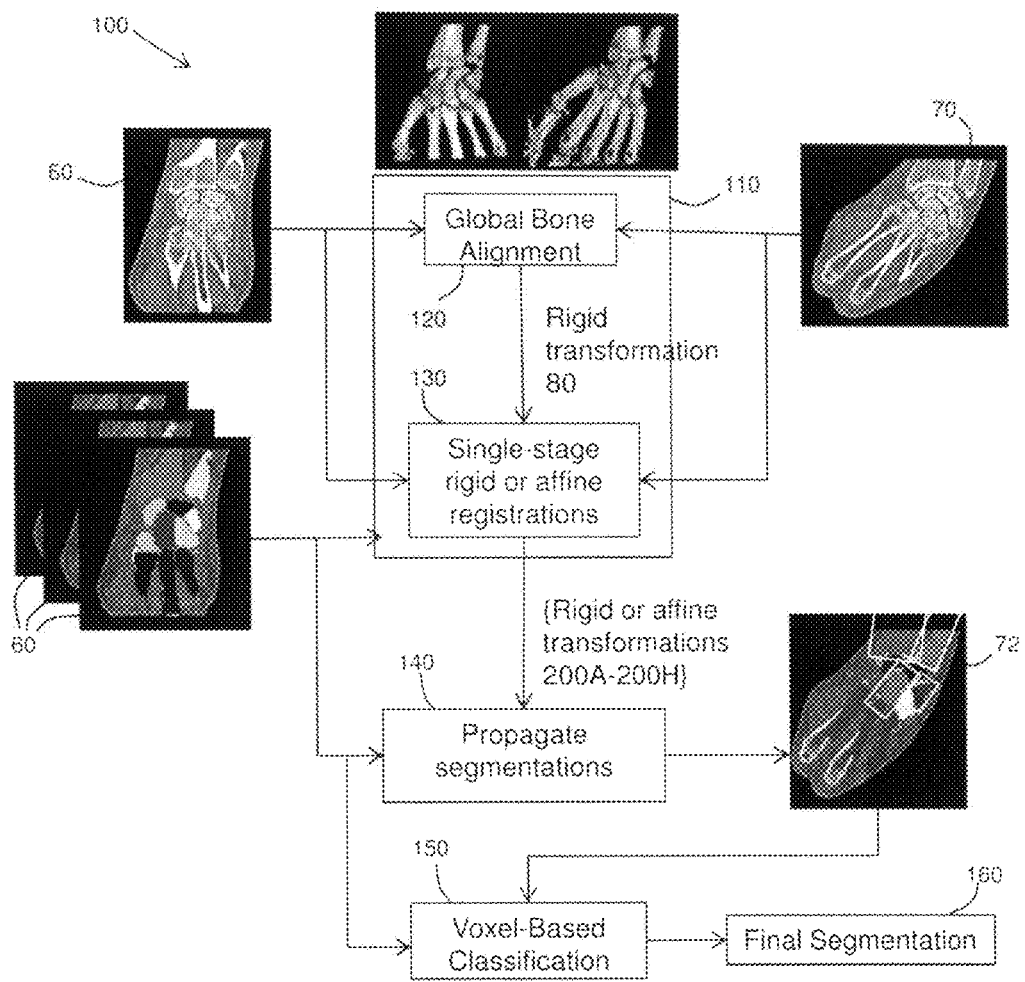
FIG. 10 is a flow chart illustrating in overview a process performed in accordance with an embodiment.

FIG. 10 is a flow-chart illustrating in overview the process of an embodiment.

In the embodiment of FIG. 10, the data receiving unit 34 receives a single imaging data set 70 from memory 30. In other embodiments, the imaging data set 70 may be received from any appropriate data store, from example a remote data store, or from the scanner 24 directly.

The single imaging data set 70 is derived from a CT scan of a patient's wrist, and relates to a single position of the patient's wrist. In other embodiments, the imaging data set 70 may be derived from a scan of any appropriate anatomical region (for example, a joint) in any modality (for example, MR, PET, SPECT, Cone Beam CT or Rotational X-ray).

Figure 14:
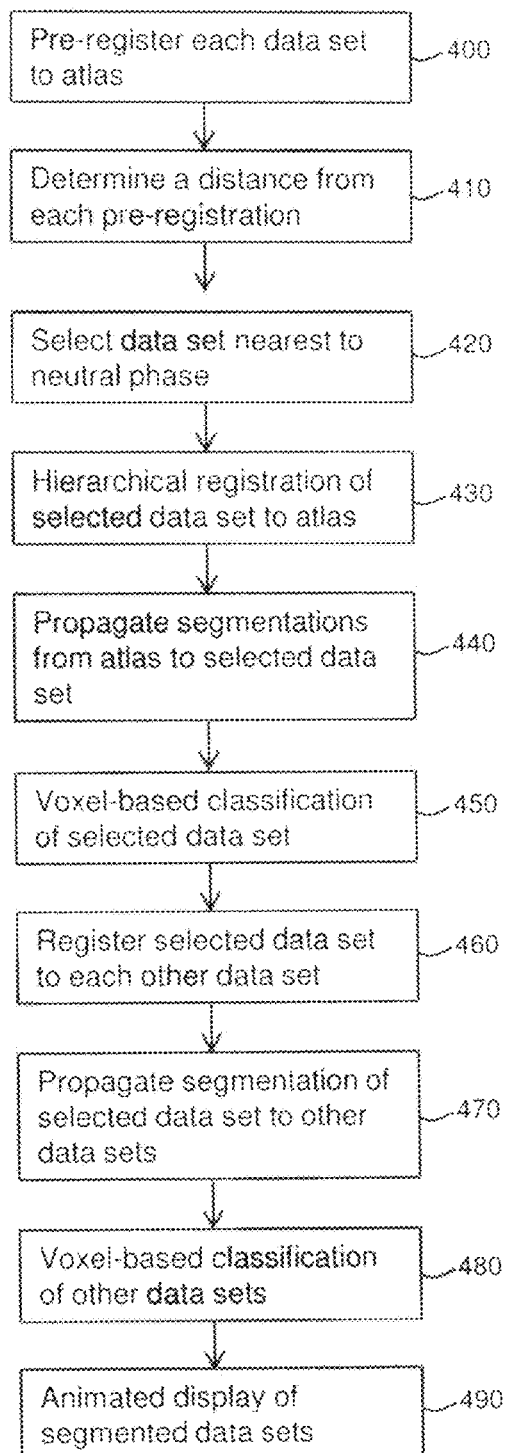
FIG. 14 is a flow chart illustrating in overview a process performed in accordance with an embodiment.

In other embodiments, the data receiving unit 34 receives volumetric imaging data comprising a plurality of imaging data sets 70, the plurality of imaging data sets 70 being derived from a matching plurality of scans of the patient's wrist. For example, the plurality of imaging data sets 70 may be derived from a kinematic study in which the wrist is imaged in a range of positions. The process discussed below with reference to FIG. 10 may be repeated or amended in embodiments in which multiple imaging data sets 70 are processed. FIG. 14 represents an embodiment in which multiple imaging data sets 70 are processed.

Imaging data set 70 comprises a plurality of voxels, each with an associated intensity value. In the present embodiment, no pre-processing has been performed on the imaging data set 70 before the imaging data set 70 is received by the data receiving unit 34. In other embodiments, pre-processing may be performed on the imaging data set 70. For example, a threshold may be applied to the imaging data set 70, for example a threshold to identify voxels which are representative of air. An initial segmentation of the imaging data set 70 may be performed, for example an initial segmentation of bone and soft tissue in the imaging data set 70.

The data receiving unit 34 receives an atlas data set 60 from memory 30. In other embodiments, the atlas data set 60 may be retrieved from any appropriate data store, for example from a remote data store. The atlas data set 60 may be stored in the data receiving unit 34.

In other embodiments, any appropriate reference data set may be used in place of an atlas data set 60. For example, a virtual anatomy may be used, or any previously segmented imaging data set or sets 70 may be used.

The atlas data set 60 comprises a representation of each individual wrist bone. For each wrist bone, the representation comprises one or more identifiers that identify the bone and indicate which voxels of the atlas data set 60 belong to that bone.

In the present embodiment, the identifiers are voxel labels. Different subsets of the voxels of the atlas are labeled as belonging to different bones of the atlas. In the present embodiment, the labels are probabilistic. Each voxel label represents a likelihood that the voxel belongs to a given bone.

In other embodiments, the identifiers associated with each wrist bone may comprise, for example, a surface or a bounding box. The representation of each wrist bone may comprise a mask, for example a probabilistic mask. It may be said that the representation of each wrist bone is a segmentation of that wrist bone in the atlas data set 60, since the representation may be used to distinguish that wrist bone from the rest of the atlas data set 60.

The atlas may be referred to as a multi-compartment atlas, since different structures (compartments) of the atlas 60 are distinguished. In the present embodiment, voxels belonging to each of the wrist bones of interest (the radius, ulna and each of the carpals and metacarpals) are individually labeled in the atlas. In other embodiments, the atlas data set 60 comprises a representation of a different anatomical region, for example another joint such as the ankle, knee, elbow or neck. A specific atlas data set 60 may be generated for each joint. In some embodiments, specific atlas data sets 60 may be generated for specific pathologies or other conditions.

The atlas data set 60 may be of a similar data type to an actual CT scan (comprising intensities for a plurality of voxels), or may be a richer or larger data type that also includes additional data, for example data comprising a vector of measurement or derived quantities at each spatial location. The atlas may be created by gathering enough actual CT data sets such that major anatomical variants are represented, and the anatomical region represented by the atlas (here, the wrist) is represented in a normal condition. The atlas may be a multiple patient atlas, created by combining CT data from multiple patients. Each set of CT data used to create the atlas may have been manually segmented by a clinical expert. The atlas data set 60 in the present embodiment is compiled during product development and embedded in the image processing apparatus 20 during manufacture.

Atlas data set 60 and imaging data set 70 are passed to the registration unit 36. The registration unit 36 performs a hierarchical rigid registration 110 of the atlas 60 and imaging data set 70. The hierarchical rigid registration 110 comprises a global bone alignment 120 followed by a plurality of single-stage rigid or affine registrations at stage 130. At least part of the stage 130 may be referred to as a multi-rigid registration, since it comprises multiple rigid registrations.

The global bone alignment 120 comprises a pre-registration. The pre-registration comprises a global rigid registration between the whole of the atlas data set 60 and the whole of the imaging data set 70. In other embodiments, a part of the atlas data set 60 may be registered with some or all of the imaging data set 70, or a part of the imaging data set 70 may be registered with some or all of the atlas data set 60.

Any suitable rigid registration method may be used. In the present embodiment, mutual information is used in the rigid registration of the atlas 60 and imaging data set 70. The rigid registration may comprise translation and/or rotation. In some embodiments, the pre-registration may be an affine registration.

The imaging data set 70 is derived from a CT scan of the patient's wrist, and the atlas data set 60 comprises a representation of a wrist which comprises identified and labeled wrist bones. In the atlas data set 60, the wrist is represented in a standard anatomical position. However, the wrist in the imaging data set 70 may be scanned in a different position and/or orientation than the representation of the wrist in the atlas data set.

The intention of the pre-registration is to perform a gross alignment of the imaging data set 70 and atlas data set 60 and thereby to obtain a rough position and orientation of the wrist in the imaging data set 70, relative to the atlas data set 60.

The pre-registration results in a rigid transformation 80 which relates the atlas 60 and imaging data set 70. The rigid transformation 80 comprises translation and/or rotation. Although in the present embodiment the pre-registration is a global rigid registration, in other embodiment an affine registration may be used.

In some embodiments, no pre-registration is performed. For example, in some embodiments it may be known that the imaging data set 70 has been acquired in such a way that the wrist in the imaging data set 70 is in approximately the same position and orientation as the wrist in the atlas data set 60 (for example, the wrist in the imaging data set 70 has been deliberately positioned in an approximation to a standard anatomical position). In such embodiments, global bone alignment 120 may be omitted from the process of FIG. 10.

The flow chart of FIG. 10 then proceeds to stage 130. Stage 130 comprises a plurality of single-stage rigid or affine registrations. Sub-stages of stage 130 are represented in the flow chart of FIG. 11.

In the present embodiment, one of the registrations in the plurality of single-stage rigid or affine registrations is an affine registration (a registration which allows scaling). In other embodiments, any of the registrations may be affine.

The plurality of single-stage rigid or affine registrations at stage 130 comprises a series of successive registrations, each of which is performed by modifying the previous registration.

An affine registration 131 is obtained by modifying global rigid registration 120. Rigid registration 132 is obtained by modifying affine registration 131 and rigid registration 134 is obtained by modifying rigid registration 132. Rigid registrations 136A to 136H are each obtained by a respective modification of rigid registration 134. These registrations are discussed in detail below with reference to FIG. 11. An aim of stage 130 is to obtain an individual registration of each of the wrist bone in the atlas to the corresponding wrist bone in the imaging data set 70.

Figure 11:
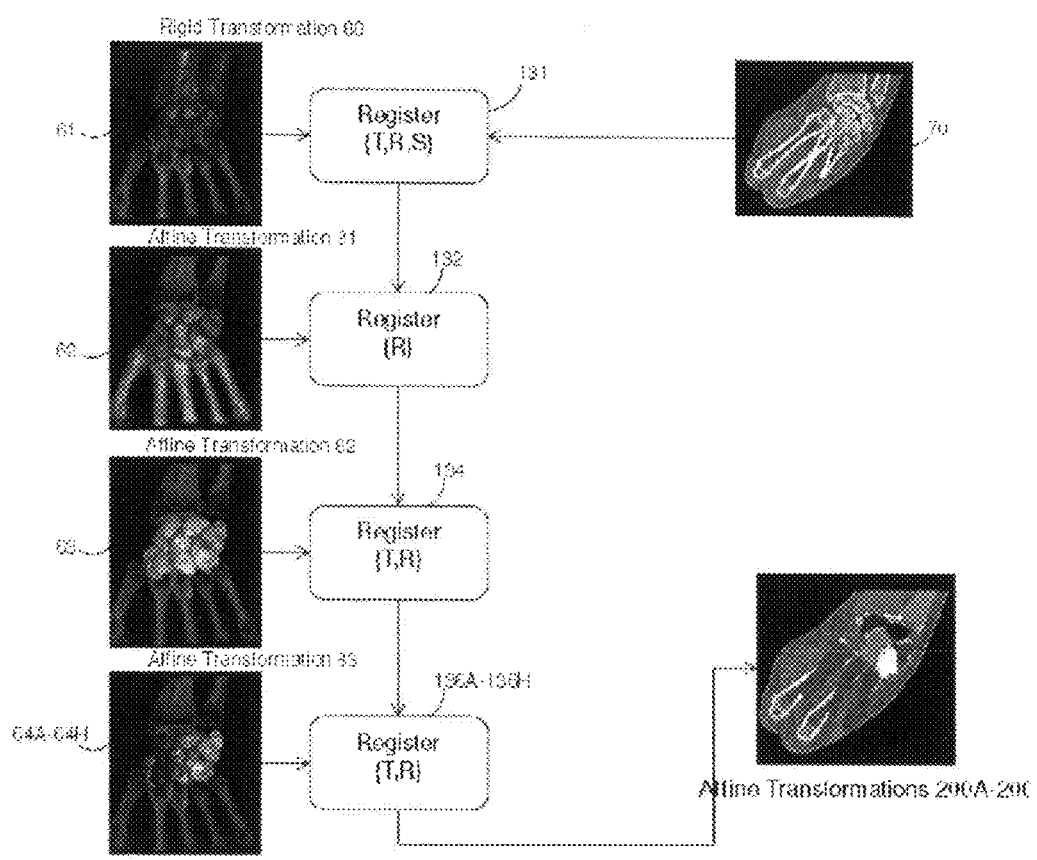
FIG. 11 is a flow chart illustrating in overview a hierarchical registration forming part of the process of an embodiment.

Turning to FIG. 11 (which describes stage 130 in more detail), the registration unit 36 receives the rigid transformation 80 resulting from the global rigid registration 120. The registration unit 36 selects a subset 61 of the atlas data set 60, where the subset 61 comprises voxels that are identified as belonging to the radius and voxels that are identified as belonging to the ulna. Subset 61 may not comprise voxels that are identified as belonging to other structures in the atlas data set 60. Subset 61 may comprise voxels in a region of interest around the radius and ulna.

The registration unit 36 performs an affine registration 131 between the subset 61 of the atlas data set and at least part of the imaging data set 70. The affine registration 122 comprises an optimization of an affine transformation between subset 61 and the imaging data set 70. The affine transformation may comprise translation, rotation and scaling.

The starting point for the affine registration 131 is the rigid transformation 80 resulting from the pre-registration. The affine registration 131 may be considered to be a refinement of the pre-registration. The optimization of the affine transformation is performed with relaxed constraints on the transformation (when compared with some constraints on transformations in later registrations in the hierarchical rigid registration 120). Constraints on the transformation may comprise limits on the amount of rotation, translation and scaling that is allowed. Relaxed constraints on the transformation may comprise, for example, limiting translation to a figure in the order of several centimeters, limiting rotation to a figure in the order of tens of degrees, and limiting scale to a figure in the order of tens of percentages. Any suitable affine registration method may be used.

In some embodiments, the imaging data set 70 is transformed using the rigid transformation 80 from the global pre-registration, and subset 61 is registered to the transformed imaging data set.

The registration of subset 61 and the imaging data set 70 results in an affine transformation 81. Affine transformation 81 may be the affine transformation that best maps the radius and ulna of the atlas data set 60 to the imaging data set 70.

In some embodiments, pre-processing is applied to the imaging data set 70 before the registration 131. For example, a threshold may be applied to the imaging data set 70 to remove voxels that are unlikely to be representative of bone. An intensity threshold may be applied to remove voxels below a certain value of intensity from the imaging data set 70 before the affine registration is performed.

In the present embodiment, the radius and ulna of the atlas data set 60 are registered first (before the registration of carpals and metacarpals described below). The radius and ulna are large bones, and it may be expected that the representation of the radius and ulna from the atlas data set may be successfully registered to the imaging data set 70 even when only a rough pre-registration (or no preregistration) has previously been performed. Also, when considering the relative movement of bones in the wrist, the radius and ulna may be considered to be static and the other bones (carpals and metacarpals) may be considered to move relative to the radius and ulna. Therefore the registration of the radius and ulna may be performed first to determine an overall position for the wrist, and other registrations may be considered relative to the affine transformation 81 obtained from the registration of the radius and the ulna.

In other embodiments, the hierarchical registration 110 may comprise a step of determining the most prominent bone or group of bones in the atlas data set 60, and the bone or group of bones that is determined to be most prominent may be registered before other bones or groups of bones. The registration of other bones or groups of bones may be performed in dependence on the registration of the most prominent bone or bones. Which registration comes first in the hierarchical registration may be dependent on the complexity and magnitude of the motion of each bone.

In the present embodiment, the imaging data set 70 is not transformed in response to the registration of the subset 61 comprising the radius and the ulna to the imaging data set 70. However, in other embodiments, the volumetric data set 70 is transformed in accordance with the affine transformation 81, so that the radius and ulna in the imaging data set 70 are aligned with the radius and ulna in the atlas data set 60. In such embodiments, the imaging data set 70 is transformed in accordance with affine transformation 81.

Once the registration unit 36 has determined affine transformation 81, the registration unit proceeds to rigid registration 132. Rigid registration 132 is a rigid registration between the representations of the carpal and metacarpal bones in the atlas data set 60 and at least part of imaging data set 70. The registration unit 36 defines a subset 62 of the atlas data set 60 which comprises voxels labeled as belonging to any of the carpal or metacarpal bones and may exclude voxels from some other structures. The registration unit 36 registers the subset 62 to at least part of imaging data set 70, using the affine transformation 81 that was obtained from the affine registration 131 of the radius and ulna as a starting point for the rigid registration 132.

In the present embodiment, the rigid registration 132 of the carpals and metacarpals is restricted to a rotation only. In the present embodiment, the constraints on the rotation angle are fairly relaxed compared to constraints in later registrations. For example, the rotation may be constrained to be within 30 degrees.

The rigid registration 132 of the carpals and metacarpals results in an affine transformation 82, which differs from affine transformation 81 by the rotation angle determined in rigid registration 132. Affine transformation 82 may be the best mapping between the representations of the carpals and metacarpals in the atlas data set 60 (when the carpals and metacarpals are considered as a group) and the imaging data set 70.

For the next rigid registration 134, the registration unit 36 defines a subset 63 of the atlas data set 60, subset 63 comprising the voxels that are labeled as belonging to the carpal bones. Subset 63 may exclude voxels that are labeled as belonging to the radius, ulna, metacarpals. The registration unit 36 registers the subset 63 to at least part of the imaging data set 70, taking affine transformation 82 as a starting point for the registration.

The registration unit 36 registers the subset 63 to the volumetric data set 70 using any appropriate rigid registration method. The rigid registration 134 may comprise both translation and rotation. The limits of the rigid registration are more constrained than those of the previous registrations 130, 132. It may be expected that a transformation of the carpal bones (as a group) will not differ by a great amount from a transformation of the group containing both carpals and metacarpals.

The output of the rigid registration 134 is an affine transformation 83 which comprises a combination of the previous affine transformation 132 and the translation and rotation determined in rigid registration 134. Affine transformation 83 may be considered to be a best mapping between the representation of the carpal bones (as a group) in the atlas data set 60 and the imaging data set 70.

As a final stage of the hierarchical rigid and affine registrations of stage 130, the registration unit 36 performs a set of individual rigid registrations 136A to 136H of the carpal bones. For each of the individual rigid registrations 136A to 136H, the registration unit 36 determines a respective subset 64A to 64H of the atlas data set 60, and registers that subset to the imaging data set 70. Each of the individual rigid registrations 136A to 136H takes as a starting point affine transformation 83 that was obtained from the previous registration 134. Each of registrations 136A to 136H may be referred to as a locally rigid registration.

As an example, we consider the rigid registration 136A of the scaphoid 10A. Registration unit 36 defines a subset 64A of the atlas data set 60, the subset 64A comprising voxels that are labeled as belonging to the scaphoid 10A. The registration unit 36 performs a rigid registration 136A of the subset 64A to the at least part of the imaging data set 70. The rigid registration 136A may comprise translation and rotation. The rigid registration takes as a starting point the affine transformation 83 which was determined by the registration 132 of the carpal bones. The limits on the rigid registration are constrained when compared to the limits on previous registrations 131, 132. It may be expected that a transformation that maps the scaphoid 10A to the imaging data set 70 may differ only in a fairly small amount from a transformation that maps all of the carpal bones to the imaging data set 70.

Any suitable rigid registration method may be used. The rigid registration 136A of the scaphoid 10A results in an affine transformation 200A which relates the representation of the scaphoid 10A in the atlas data set 60 to the imaging data set 70. Affine transformation 200A differs from affine transformation 83 by the translation and rotation determined in the rigid registration 136A.

Similar rigid registrations are performed for each of the other carpal bones 10B to 10H.

In the present embodiment, the same rigid registration method is used for all the individual rigid registrations 136A to 136H. In other embodiments, different registration methods may be used for each of the carpals. In some embodiments, different constraints may be used on the registration of one of the carpal bones from the constraints used on the registration of another of the carpal bones.

In the present embodiment, each individual registration 136A to 136H is performed by modifying affine transformation 83. In other embodiments, the individual registration of at least one of the carpal bones may be obtained by modifying an individual registration of another of the carpal bones. For example, once the individual registration 136A of the scaphoid 10A has been obtained, the registration unit 36 may use the transformation 200A that has been obtained from the registration 136A of the scaphoid 10A as a starting point for the registration of the lunate 10B. Each carpal bone may be registered based on the registration 134 of the group of carpal bones or on the registration of another one or more of the carpal bones, for example on the registration of a neighboring one or more carpal bones.

The output of registrations 136A to 136H (and therefore the output of the single-stage hierarchical rigid registration 130) is the set of affine transformations 200A to 200H, each of which relates a respective carpal bone in the atlas data set 60 to the volumetric data set 70.

In any of registrations 131 to 136H, a region of interest may be defined in the atlas data set and the registration may be performed with respect to the region of interest in the atlas data set. In any of registrations 131 to 136H, a region of interest may be defined in the imaging data set and the registration may be performed with respect to the region of interest in the imaging data set.

In the hierarchical rigid and affine registrations of stage 130, progressively smaller groups of structures are registered in successive registrations. The earlier registrations in the hierarchical rigid registration are performed on large groups, which may have the effect of obtaining a robust registration due to a larger amount of data being present. The later registrations may be considered to be refinements of the earlier registrations.

If an attempt was made to register one of the small bones in the wrist, for example the scaphoid 10A, to the imaging data set 70 without taking as a starting point a previous registration of a group of structures, it is possible that such a registration may fail. The wrist bones may be of reasonably similar shapes and sizes and are closely grouped in space. By first registering at least one larger group of structures (the wrist bones, and then the carpal bones), an approximate transformation is achieved which may then be refined by the registration of the single wrist bone, for example the scaphoid 10A. By using rigid registrations, the shapes of bones are preserved.

To obtain individual registrations of individual bones, a multi-compartment atlas is used which comprises representations of individual bones, in which each bone is individually labeled. Any suitable representation may be used, as long as individually bones can be individually distinguished. The hierarchical registration depends on the spatial information provided by the atlas.

Although in the present embodiment, the registration unit 36 defines subsets of the atlas data set to be used in registrations 131, 132, 134 and 136A to 136H, in other embodiment the subsets may be pre-existing and may not need to be defined. In some embodiments, separate data sets may be stored, each of which comprises representations of particular bones. For example, one data set may comprise the representation of the radius and of the ulna, and may be used in place of subset 61.

Transformations have been obtained for each of the bones in the wrist. Each transformation may be represented as a matrix.

In the present embodiment, an initial registration of the radius and ulna is followed by registrations of successively smaller groups of wrist bones. In other embodiments, the imaging data set 70 and atlas 60 represent a different joint other than the wrist, and may represent tissues other than bone. In general, an initial registration of at least part of the atlas data set 60 is followed by at least one further registration of a subset of the atlas data set 60. The at least part of the atlas data set 60 comprises a first anatomical structure or group of anatomical structures, and the subset of the atlas data set comprises a second anatomical structure or group of anatomical structures. A group of structures may be an anatomically adjacent plurality of structures, for example the group of wrist bones, the group of metacarpals, the group of carpals, or a group comprising the radius and ulna. In some embodiments, the at least part of the reference data set is the entire atlas data set 60 and comprises all the anatomical structures in the atlas data set 60. The first anatomical structure or group of anatomical structures may be neighboring to the second anatomical structure or group of anatomical structures.

Which anatomical structure or structures are registered first may depend on one or more factors. In some embodiments, larger structures are registered before smaller structures. In some embodiments, progressively smaller groups are registered. Some joints, for example the elbow, comprise a hinged structure. In embodiments involving such joints, the initial registration may be a registration of the bone or bones on one side of the hinge, and the at least one further registration may comprise a registration of the bone or bones on the other side of the hinge. The second structure or group of structures may be a structure or group of structures that is expected to undergo significant motion with respect to the first structure or group of structures when the joint is moved.

Turning again to FIG. 10, the affine transformations 200A to 200H that were determined in the hierarchical rigid registration 110 are passed from the registration unit 36 to the segmentation unit 38. In the present embodiment, the affine transformation 81 resulting from the affine registration 131 of the radius and ulna and the affine transformation 82 resulting from the registration 132 of the carpals and metacarpals are also passed from the registration unit 36 to the segmentation unit 38.

At stage 140, the segmentation unit 40 propagates segmentations from the atlas data set 60 to the imaging data set 70. That is, the segmentation unit 40 uses the representations of individual bones in the atlas data set 60 to determine provisional segmentations of those bones in the imaging data set 70.

The representations of individual bones in the atlas data set 60 may be referred to as segmentations of those bones in the atlas data set 60, the atlas data set 60 having been manually segmented so that individual bones may be identified and labeled.

The segmentation unit 40 maps the representation of the radius in the atlas data set 70 onto the imaging data set 70. In the present embodiment, the segmentation unit 40 maps the voxels that are labeled as radius in the atlas data set 60 onto the imaging data set 70 using the affine transformation 81 that was determined from registration 131 of the radius and ulna. The segmentation unit 40 provisionally labels as radius voxels the voxels of the imaging data set 70 onto which the representation of the radius is mapped.

The segmentation unit maps the voxels that are labeled as ulna in the atlas data set 60 to the imaging data set 70 using the affine transformation 81 that was determined from the registration 131 of the radius and ulna. The segmentation unit 40 provisionally labels as ulna voxels the voxels of the volumetric data set 70 onto which the representation of the ulna is mapped.

The segmentation unit maps the voxels that are labeled as metacarpals in the atlas data set 60 to the imaging data set 70 using the affine transformation 82 that was determined from rigid registration 132 of the carpals and metacarpals. (using a transformation that is relatively rotated with respect to the transformation used for the radius and ulna.) In the present embodiment, each metacarpal is individually labeled in the atlas data set 60. The voxels from each metacarpal are mapped onto the volumetric data set, and the voxels in the imaging data set 70 that correspond to the voxels of that individual metacarpal are provisionally labeled as belonging to that individual metacarpal.

The segmentation unit 40 maps voxels of each carpal 10A to 10H to the imaging data set 70 using a respective individual affine transformation 200A to 200H. Since each carpal 10A to 10H may have a different transformation, the mapping takes into account movement of the carpal bones relative to each other with respect to the anatomical positions present in the atlas data set 60.

For each carpal bone 10A to 10H, the voxels that are labeled as belonging to that carpal bone in the atlas data set 60 are mapped on to the imaging data set 70, and the voxels in the imaging data set 70 that correspond to the mapped voxels are provisionally labeled as belonging to that carpal bone 10A to 10H.

A data set 72 is thereby obtained in which voxels are provisionally labeled as belonging to each of the bones of the wrist. Stage 140 may be described as a registration-based segmentation, since each of the anatomical structures which is represented in the atlas data set 60 is mapped onto the imaging data set 70 to provide a provisional segmentation of corresponding structures in the imaging data set 70.

In the present embodiment, only one segmentation of the atlas data set 60 is propagated onto the imaging data set 70 at stage 140. In other embodiment, the atlas data set 60 comprises multiple segmentations. For example, the atlas data set 60 may comprise a plurality of data sets, each of which is segmented. Stage 140 may be repeated for each segmented data set in the atlas data set 60.

In the present embodiment, the representation of the structures in the atlas data set 60 is probabilistic. For example, different voxels within the same structure may be labeled as having different likelihoods of belonging to that structure. The likelihoods are propagated to the imaging data set 70 at stage 140, resulting in a provisional segmentation of imaging data set 70 which includes likelihood data.

At stage 150, the segmentation unit 40 performs a classification of voxels in the volumetric data set using the provisionally labeled data set 72. The classification comprises expectation maximization, MAP (maximum a posteriori) classification and morphological cleaning, as described in further detail below.

The atlas-based expectation maximization (EM) algorithm is used to estimate tissue models (based on intensity) within the underlying data. The closeness of a measured voxel's intensity to the tissue models is presented as a likelihood. A spatially-aware EM algorithm allows discrimination between similar intensity profiles at different positions. A spatially-aware EM algorithm may provide more accurate estimates of distribution parameters that an EM algorithm that is not spatially aware.

MAP classification provides a refinement of the registration-based segmentation that was performed in stage 140. MAP classification may in some circumstances lead to a substantial increase in segmentation accuracy. A Bayesian framework is used in which:

$$P(l_x=k|i_x) \propto P(i_x|l_x=k)P(l_x k) \qquad \text{(Equation 1)}$$

where $l_x$ is the label at voxel x, k is the structure to be segmented and $i_x$ is the intensity at voxel x. $P(l_x=k)$ is the likelihood with which voxel x is provisionally labeled belonging to structure k, and is obtained from the segmentation propagation of stage 140. $P(i_x|l_x=k)$ is the likelihood of a given intensity $i_x$ at voxel x given that voxel x is labelled as belonging to structure k. This likelihood is calculated using the atlas-based expectation maximization algorithm.

The output of the MAP classification is a refined set of voxel likelihood data. The segmentation unit 40 performs morphological cleaning operations on the refined likelihood data. The morphological cleaning operations may comprise, for example, at least one of a morphological open, a morphological close, a connected-component analysis and a morphological filling. The aim of the morphological cleaning is to remove loosely connected voxels to arrive at a smooth final output (for example, smooth structure boundaries). Morphological cleaning may in some circumstances lead to a substantial increase in segmentation accuracy, particularly at the edges of objects.

The output of the voxel-based classification of stage 150 is a final segmentation 160 of the imaging data set 70. In the final segmentation 160, each voxel is assigned a label. For example, a first subset of voxels in the volumetric data set is labeled as radius, a second subset as ulna, and respective subsets for each carpal and metacarpal. A further subset may also be determined for which the label is 'none of the above'. Alternatively, no label may be assigned to voxels which are not determined to be part of one of the structures of interest (here, the wrist bones including the radius and ulna).

A modified imaging data set may be determined which includes the determined labels, or the labels may be stored as a separate data set along with the imaging data set 70.

Figure 12:
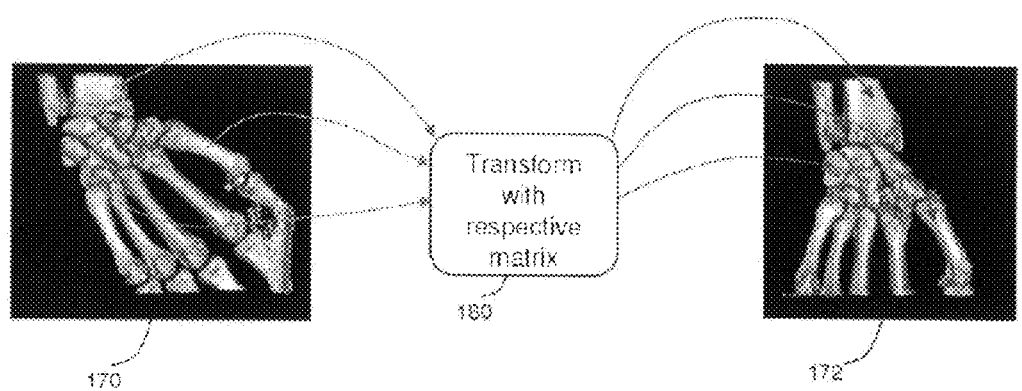
FIG. 12 is an illustration of the transforming of a wrist image.

In one embodiment, illustrated in FIG. 12, the final segmentation 160 of the imaging data set 70 is used to transform the labeled structures of the imaging data set 70 (here, the wrist bones) into a standard anatomical view.

Image 170 is a rendered image of an imaging data set 70. It may be seen that the wrist in this imaging data set 70 is not in a standard anatomical position (which may be described as neutral phase).

At stage 180, the bones that have been segmented in the volumetric data set 70 are transformed by applying the affine transformations obtained from the process of FIG. 11 (each of which may be represented as a respective transformation matrix). The radius and ulna are transformed in accordance with affine transformation 81. The metacarpals are transformed in accordance with affine transformation 82. Each of the carpals is transformed in accordance with the appropriate one of affine transformations 200A to 200H.

In the present embodiment, the imaging data set 70 is not transformed at any stage of the process of FIGS. 10 and 11 and all transformations are performed after the final segmentation 160 has been determined. In other embodiments, the entire imaging data set 70 may be transformed after the pre-registration in accordance with rigid transformation 80 and/or after the global rigid alignment 120 in accordance with affine transformation 81. Further registrations may be performed on the transformed imaging data set.

In the present embodiment, the segmentations of all the bones are performed after the full hierarchical registration 110 has been performed. In other embodiments, the segmentation propagation 140 and voxel-based classification 150 may be performed earlier in the process of FIG. 10 for some bones. For example, a segmentation of the radius and ulna comprising a segmentation propagation 140 and voxel-based classification 150 may be performed as soon as the affine transformation 81 has been obtained.

By transforming each of the bones with an appropriate transformation, the bones that have been segmented from bones in imaging data set 70 are transformed into a standard anatomical position. Image 172 is a rendered image in which the bones shown in image 170 have been transformed into standard anatomical position. By displaying the bones in a standard anatomical position, it may become easier for a clinician to observe any malformations in the bones.

In some circumstances, pathology, trauma and scanning condition can hinder a clear visualization of patient anatomy. By presenting data in a standard anatomical view, the data may become easier to understand.

In some embodiments, bones in imaging data set 70 may be transformed into an anatomical arrangement that is not the anatomical arrangement of the atlas data set 60, for example an arrangement that is not a neutral phase arrangement. In some embodiments, bones may be transformed into an exploded or disarticulated arrangement. The rendering unit 40 may render an exploded or disarticulated arrangement of the bones of imaging data set 70. Presentation of patient data using techniques that are typical of illustrative anatomical drawings may shed further light on pathologies. The method of FIG. 10 may be used to automate or partially automate the presentation of patient data in illustrative views. Such presentation may be laborious and time-consuming when performed manually.

Figure 13A:
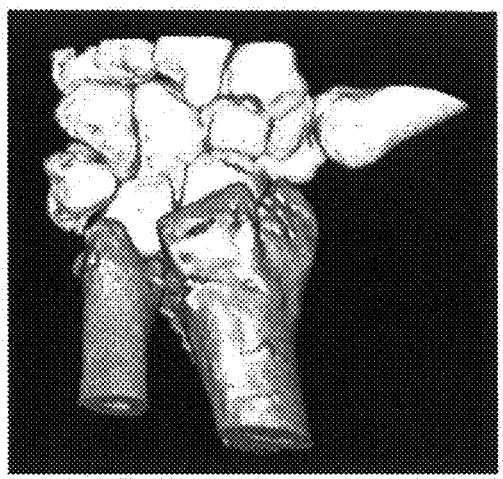
FIGS. 13*a* shows a rendered image in which the radius and ulna are presented.
Figure 13B:
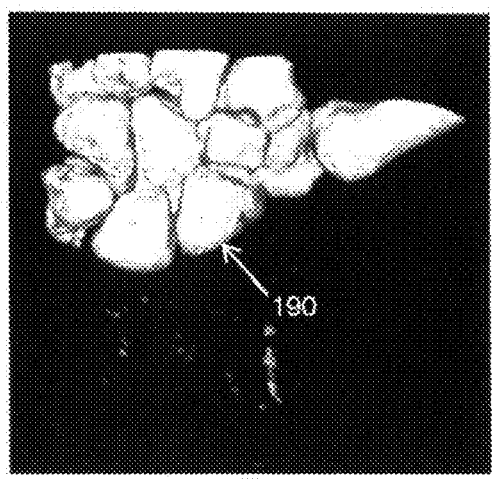
FIG. 13*b* shows a corresponding rendered image in which the radius and ulna have been removed.

In one embodiment, illustrated by FIGS. 13*a* and 13*b*, the rendering unit 40 renders an image from the imaging data set 70 (which may or may not be transformed into anatomical position). Since each bone has been individually segmented from imaging data set 70, it is possible for each bone to be treated individually in the image. For example, different bones may be rendered in different colors or using different visual effects, or only some of the bones may be rendered in an image with other bones being omitted.

The rendered image is displayed on display screen 26. Each bone in the rendered image is selectable by a user. The user may select each bone by, for example, clicking on the bone using a mouse 28.

In the image of FIG. 13*a*, a user has clicked on each of the radius and the ulna to select the radius and the ulna. The rendering unit 40 has then re-rendered the image such that the selected bones (radius and ulna) are colored in a different color from the non-selected bones in FIG. 13*a*.

The user then gives a command to remove the bones that they have selected. For example, the user may give a text command or click on a button. The rendering unit 40 re-renders the image such that the selected bones are not displayed in the image (as illustrated in FIG. 13*b*). Such a selective display is possible due to the segmentation of the imaging data set 70.

By segmenting the imaging data set 70, particular bones of the wrist may be selectively displayed or selectively removed from an image. By displaying only some of the wrist bones, or only one of the wrist bones, it may be possible for a clinician to obtain views that may not be possible from conventional images in which the bones have not been individually segmented. For example, the clinician may be able to view bone surfaces that may not be visible when all the bones are present. Arrow 190 of FIG. 13*b* indicates a bone surface that has become visible by removing the segmented radius and ulna from the rendered image of the wrist. If an image is rendered from an unsegmented volumetric data set, or a data set from which all bone is segmented as a whole without individual bones being distinguished, then it may not be possible to render an image in which surface 190 is visible.

In the embodiment described above with reference to FIGS. 10 and 11, the volumetric imaging data received by the data receiving unit 34 comprises a single medical imaging data set 70 representative of a single image of the wrist of the patient.

In other embodiments, the volumetric data set comprises a series of medical imaging data sets 70 that are obtained from a 4D kinematic study of the wrist of a patient (in other embodiments, the 4D kinematic study may be a 4D kinematic study of any joint of a patient). In a 4D kinematic study of the wrist, many successive images are taken of the patient's wrist while the wrist performs a particular motion. The images may then be rendered to produce an animated image of the wrist motion.

FIG. 14 is a flow chart illustrating in overview the process of an embodiment in which data from a 4D kinematic study is processed.

A 4D kinematic study of the wrist of a patient is performed in which the patient moves the wrist in a side-to-side rotation in the plane of the hand (radial-ulnar deviation). The CT scanner 24 obtains volumetric imaging data which comprises multiple imaging data sets 70, each representative of a particular position of the wrist. The positions of the wrist cover the full range of motion of the wrist in the radial-ulnar sense.

At stage 400, the data receiving unit 34 receives all of the imaging data sets 70. The data receiving unit 34 passes the imaging data sets 70 to the registration unit 36. The registration unit 36 performs a respective pre-registration between each of the imaging data sets 70 and the atlas data set 60. Each pre-registration comprises a global rigid registration, comprising translation and rotation. The registration unit 36 determines an optimum rigid transformation 81 for each data set by optimizing a similarity measure. The determined rigid transformation is the transformation required to transform the data set into the coordinate space of the atlas data set 60.

At stage 410, the registration unit 36 transforms each of the imaging data sets 70 in accordance with its determined rigid transformation to obtain a transformed data set. For each of the imaging data sets 70, the registration unit 36 determines a registration measure, in this case a distance between the data set and the transformed data set, which represents an amount of transformation represented by the registration.

In the present embodiment, for each imaging data set 70, the registration unit 36 selects a set of points in the imaging data set 70 and determines a Euclidean distance between the set of points in the imaging data set 70 and the transformed version of the set of points in the transformed data set. The Euclidean distance may be considered to be representative of the extent to which the data set is transformed, and may be taken as the registration measure in this case.

In other embodiments, a different measure of distance may be used as the registration measure. In some embodiments, the data sets are not transformed. In some embodiments, only a set of points is transformed. Any suitable method may be used for determining a respective distance for each of the data sets.

At stage 420, the registration unit 36 selects the data set having the smallest Euclidean distance or other registration measure. The selected data set is assumed to be representative of the neutral phase of motion. In the neutral phase of motion, the wrist will be closest to the anatomical position of the wrist that is represented in the atlas data set 60. Therefore a smaller translation and/or rotation may be required to register to the atlas data set 60 the imaging data set 70 that is representative of the neutral phase of motion than is required to register any other data set to the atlas data set 60.

At stage 430, the registration unit 36 performs a hierarchical registration of the selected data set and the atlas data set 60. The hierarchical registration comprises an affine registration 131 of the radius and ulna, a rigid registration 132 of the carpals and metacarpals, a rigid registration 134 of the carpals and rigid registrations 134A to 134H of each of the carpals. Each successive registration is a modification of the previous registration.

At stage 440, the segmentation unit 38 propagates the individual segmentations of the wrist bones from the atlas data set 60 to the selected data set. The segmentation unit 36 thereby obtains a provisional segmentation of the selected data set. Voxels in the selected data set are provisionally labeled as belonging to different ones of the wrist bones.

At stage 450, the segmentation unit 38 performs a voxel-based classification of the selected data set based on the provisional labeling obtained at stage 440. The voxel-based classification comprises expectation maximization, MAP classification and morphological operations including connected component labeling. The voxel-based classification results in a final segmentation of the selected data set.

At stage 460, the registration unit 36 registers the selected data set to each of the other imaging data sets. The registration of the selected data set to each of the other imaging data sets may comprise affine or rigid registration. The registration of the selected data set to each of the other imaging data sets may comprise multiple successive registrations. The registration of the selected data set to each of the other imaging data sets may comprise hierarchical registration.

At stage 470, the segmentation unit 38 propagates the final segmentation of the selected data set (as obtained at stage 450) to each of the other imaging data sets. The segmentation unit 38 thereby obtains a provisional segmentation of each of the other imaging data sets.

At stage 480, the segmentation unit 38 performs a voxel-based classification of each of the other imaging data sets to obtain a final segmentation of each of the other imaging data sets 70. A final segmentation is thereby obtained for every one of the imaging data sets 70 that was received and pre-registered at stage 400.

In the embodiment of FIG. 14, a single one of the multiple imaging data sets 70 is selected and the selected data set is registered to the atlas data set 60 and segmented by propagating the segmented structures of the atlas data set 60. The selected data set is registered to each of the other imaging data sets and the segmentation of the selected data set is propagated to the each of the other imaging data sets.

However, in other embodiments, the registration unit 34 individually registers each of the multiple imaging data sets 70 to the atlas data set 60 using hierarchical registration. The segmentation unit 36 propagates the segmentations of the atlas data set 60 to each of the multiple imaging data sets 70.

In other embodiments, some of the imaging data sets 70 may be selected to be hierarchically registered to the atlas data set 60 and others may each be registered to one of the selected data sets.

Although in the embodiment of FIG. 14 the imaging data set 70 that is segmented is the one that is determined to be nearest to neutral phase, in other embodiments it is not required that a neutral phase or near-neutral phase imaging data set 70 is present. A hierarchical atlas-based approach may provide a result that is robust to wrist posture.

At stage 490, the rendering unit 40 renders an animated display from the multiple imaging data sets 70 using the segmentations that have been determined at stage 440 and 480. The animated display comprises a plurality of image frames, each of which is a rendering of a respective imaging data set 70. Since each bone is individually segmented, the bones may be rendered so as to distinguish each bone, for example by rendering each bone in a different color. Certain bones may be omitted from the display, by default or in response to a user selection.

In the present embodiment, the animated display is rendered such that the position of one of the bones in the animated display is held static across all frames, and the other bones are presented as moving relative to the static bone. The static bone may be referred to as a locked bone, and the presentation of images in which motion occurs relative to one locked bone may be referred to generally as bone locking.

By rendering the animated display such that one bone is held static, the clinician may obtain additional information about the relative position of the bones that may not be available if each image was rendered in its original position without registration or transformation. The movement of the wrist may be a complex movement in which all of the bones may move. By holding one of the bones static, it may be easier to see the relative motion between that bone and a selected other bone or bones, which can give insight into any problems with the motion and may be helpful in describing the dynamics of the surrounding bones and ligaments.

By holding one of the bones static, a visualization may be obtained which is not a realistic visualization in the sense that it does not look like a natural wrist movement, but may be clinically useful.

By applying the method of FIG. 14, all the bones in the wrist may be automatically detected and any one of the bones may be locked. Kinematic analysis may be automatically performed and presented per individual bone.

In some embodiments, the segmentation unit 36 is further configured to perform bone measurements on some or all of the imaging data sets 70. In some embodiments, a set of measurements are defined on the atlas data set 60. The set of measurements may comprise a set of lengths and angles that are anatomically defined. For example, the length of a bone may be defined by defining a line between two points on the bone and taking the length of the line. The angle between two bones may be defined by defining two lines relating points on the bones, and taking the angle between them.

The defined bone measurements are propagated from the atlas data set 60 to at least one imaging data set 70 using appropriate transformations (for example, 81, 82, 83 to any of 200A to 200H, depending on the bone or bones on which the measurements are defined). In the present embodiment, the measurements are then propagated from one imaging data set 70 to the other imaging data sets 70. In other embodiments, measurements are propagated from the atlas data set 60 to each of the imaging data sets 70.

Measurements may thereby be obtained for each of the imaging data sets 70 in a series of imaging data sets 70. Such measurements may be used to show how measurements (for example, a distance between bones or an angle between bones) change with joint motion.

In some embodiments, a first set of measurements is obtained for all the imaging data sets 70 of a first 4D kinematic study. A second set of measurements is then obtained for all the imaging data sets 70 of a second 4D kinematic study. In some embodiments, the first 4D kinematic study is taken before surgery, and the second 4D kinematic study is taken after surgery, The first set of measurements are compared with the second set of measurements to quantify changes in joint motion.

Although embodiments above describe rendering of images after hierarchical registration, in some embodiment no rendering may be performed. The apparatus of FIG. 6 may not include a rendering unit 40. For example, the process of FIG. 14 (minus stage 490) may be used to hierarchically register a set of imaging data sets 70 from a 4D kinematic study. Measurements may be determined and stored without any rendering being performed.

Automatic and precise alignment of patient data to anatomical position may be obtained. Such automatic and precise alignment may be needed in the case of poor scanning conditions. Such automatic and precise alignment may also be needed where a limited range of patient movements are available, for example where the wrist of the patient may not be moved into the full range of positions that are normally acquired.

By performing local rigid registration, it may be ensured that there is no deformation to bones resulting from the registration.

The phase closest to the neutral phase may be identified in 3D kinematic studies.

By analyzing data from a 4D kinematic study, multiple ligamentous injuries and instabilities may be studied. Examples of injuries that may be studied include injuries to the Triangular Fibrocartilage Complex (TFCC), subtalar luxation, Distal Radial Ulnar Joint Instability (DRUJI) and SLAC (scaphoid lunate advanced collapse) injuries. 4D kinematic studies of different joints may be performed, for example the wrist, ankle, shoulder, hip, elbow, acromioclavicular or temporomadibular joint.

Carpal instability is an example of a condition that may be studied. The current understanding and definition of carpal instability may be considered to be between 25 and 80 years old. Carpal instability may be due to disruption of the interosseous ligaments that connect and stabilize the carpal bones. There is a widespread amount of clinical findings and symptoms for midcarpal and carpal instability. However, because of the dynamic and elusive nature of carpal injuries, there may at present be little radiographic evidence to determine the underlying cause of a midcarpal instability. Severe carpal disruptions may be injuries that are frequently missed. With degenerative conditions, early diagnosis is important. Methods according to at least some embodiments may improve identification, diagnosis and treatment of underlying causes of carpal instability and other conditions.

The current standard for diagnosing most joint instabilities is arthroscopy. Arthroscopy is a highly invasive procedure. Application of methods describe above may minimize the number of cases in which arthroscopy is required.

Certain embodiments comprise a medical imaging method comprising receiving a volumetric data set representing one or more anatomies, receiving a multi-object anatomical atlas of the anatomy, and performing a method to identify, label, register and segment individual tissues, based on multi-rigid hierarchical registration of the atlas. The multi-rigid hierarchical registration of the atlas comprises the following steps; determining the most prominent group of objects in the atlas (which may be the entire atlas), a rigid registration of the most prominent group of objects in the atlas to the volumetric data set, applying the result of the registration to the whole data set (not just the objects) to give a general orientation, performing hierarchical registration of progressively smaller or neighboring groups of objects, applying registration to each of the objects, and propagating registered segmentations to nearby voxels in the volumetric imaging data set using voxel-based classification.

The data set may be a 4D dynamic CT study. The results of the method may be used to align patient data to anatomical position. The volumetric data set may represent a joint, such as wrist, ankle, neck, elbow, knee, etc.

A hierarchical registration method may be determined for each joint, which may comprise a series of successive registrations, each successive registration comprising a modification of the previous registration. Each of the successive registrations may be performed with respect to representations of different anatomical structures in the atlas data set (or other reference data set). The atlas data set (or other reference data set) contains information about the relative positions of the bones in the joint and their relationship (for example, which bones are connected to each other and which bones are expected to undergo relative rotation on movement of the joint).

A registration of a group of structures may be followed by a registration of a sub-group of the group of structures, or a registration of a single member of the group of structures. A registration of one or more bones may be followed by a registration of an adjacent bone. For each joint, the order of registration may be determined with reference to the size of bones in the joint and the degree of relative motion of the bones.

Embodiments have been described above with reference to the wrist. In other embodiments, hierarchical registration may be performed with respect to any joint in the body. For example, hierarchical registration may be performed on the wrist, ankle, shoulder, hip, elbow, acromioclavicular or temporomadibular joint.

Embodiments have been described in which bones have been identified and labeled in one or more imaging data sets 70. In further embodiments, other tissues may be identified and labeled. Structures that may be identified and labeled may include, for example, ligaments, tendons, organs, muscles or vessels.

Embodiments have been described above with reference to particular rigid and affine registrations. In other embodiments, affine registrations may be substituted for rigid registrations. Rigid registrations may be substituted for affine registrations. In some embodiments, one or more non-rigid registrations may be substituted for one or more of the rigid or affine registrations described above.

Registration of any appropriate medical imaging data to a suitable atlas may be performed, where medical includes veterinary. Medical imaging data may comprise, for example, CT, MR, PET, SPECT, rotational X-ray or cone beam CT data. Medical imaging data may comprise imaging data taken from one or more scans of a patient or other subject.

Whilst particular units have been described herein, in alternative embodiments functionality of one or more of these units can be provided by a single unit, or functionality provided by a single unit can be provided by two or more units in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An imaging data processing apparatus, comprising:
processing circuitry configured to obtain a hierarchical registration between a reference data set and volumetric medical imaging data, the reference data set comprising a plurality of anatomical structures, wherein the obtaining of the hierarchical registration comprises
selecting, in the reference data set, a first anatomical structure or group of anatomical structures and a second, different anatomical structure or group of anatomical structures, wherein the first anatomical structure or group of anatomical structures is larger and/or more static than the second anatomical structure or group of anatomical structures;
performing a first registration to obtain a first rigid or affine transformation between a first subset of the reference data set comprising the first anatomical structure or group of anatomical structures and at least a first part of the volumetric medical imaging data;
segmenting the first anatomical structure or group of anatomical structures in the volumetric medical imaging data in dependence on the first registration;
performing a second registration to obtain a second rigid or affine transformation between a second subset of the reference data set comprising the second anatomical structure or group of anatomical structures and at least a second part of the volumetric medical imaging data, wherein the second rigid or affine transformation is obtained by refining the first rigid or affine transformation; and
segmenting the second anatomical structure or group of structures in the volumetric medical imaging data in dependence on the second registration, such that the first anatomical structure or group of anatomical structure and the second anatomical structure or group of structures are segmented in the volumetric medical Imaging data using different, successive registrations.

2. The apparatus according to claim 1, wherein the hierarchical registration comprises a series of successive registrations including the first and second registrations, each successive registration comprising a modification of the initial registration or of a preceding one of the successive registrations.

3. The apparatus according to claim 2, wherein each of the successive registrations is performed with respect to a different subset of the reference data set.

4. The apparatus according to claim 2, wherein the plurality of anatomical structures comprises a plurality of wrist bones, the first registration is performed first and comprises a registration of at least one of a radius and an ulna, and the series of successive registrations comprises a registration of a group of metacarpal bones and carpal bones, and a registration of at least one carpal bone performed by modifying the registration of the group of metacarpal bones and carpal bones.

5. The apparatus according to claim 1, wherein the hierarchical registration comprises a plurality of individual registrations, each of the individual registrations comprising a registration of a respective anatomical structure or group of anatomical structures.

6. The apparatus according to claim 5, wherein the segmenting of the volumetric medical imaging data in dependence on the hierarchical registration comprises segmenting each anatomical structure or group of structures in the volumetric medical imaging data in dependence on the individual registration of that anatomical structure or group of anatomical structures.

7. The apparatus according to claim 5, wherein the processing circuitry is further configured to align each said anatomical structure or group of anatomical structures to the reference data set in dependence on the individual registration of that anatomical structure or group of anatomical structures.

8. The apparatus according to claim 1, wherein the plurality of anatomical structures comprises bones of a joint.

9. The apparatus according to claim 8, wherein the hierarchical registration comprises a series of successive registrations including the first and second registrations, wherein the successive registrations are performed with respect to successively smaller bones or groups of bones.

10. The apparatus according to claim 1, wherein the first anatomical structure or group of anatomical structures is neighboring to the second anatomical structure or group of anatomical structures.

11. The apparatus according to claim 1, wherein the volumetric medical imaging data comprises a plurality of medical imaging data sets obtained from scans of a joint, each corresponding to a different position of the joint.

12. The apparatus according to claim 11, wherein the obtaining of the hierarchical registration by the processing circuitry comprises performing a respective hierarchical registration between the reference data set and each of the plurality of medical imaging data sets.

13. The apparatus according to claim 11, wherein the obtaining of the hierarchical registration by the processing circuitry comprises performing a hierarchical registration between the reference data set and a selected one of the plurality of medical imaging data sets, and wherein the processing circuitry is further configured to register each other one of the medical imaging data sets to the selected medical imaging data set.

14. The apparatus according to claim 13, wherein the processing circuitry is further configured to select the selected medical imaging data set by registering each of the plurality of medical imaging data sets to the reference data sets, determining a registration measure for each registration, and selecting the one of the plurality of data sets having the smallest registration measure.

15. The apparatus according to claim 11, wherein the segmenting of the volumetric medical imaging data by the processing circuitry comprises segmenting a selected at least one anatomical structure in each of the medical imaging data sets;
wherein the processing circuitry is further configured to align the medical imaging data sets such that a position of the selected at least one anatomical structure is substantially constant in the aligned medical imaging data sets; and wherein the processing circuitry is configured to render a series of images from the aligned medical imaging data sets, thereby obtaining a series of images in which other anatomical structures appear to move relative to the selected at least one anatomical structure, which appears to remain substantially static.

16. The apparatus according to claim 1, wherein the processing circuitry is further configured to render an image from the segmented first anatomical structure or group of anatomical structures and the second anatomical structure of group of anatomical structures, the rendered image comprising a least one of an exploded view, a disarticulated view, a standard anatomical view, a neutral phase view, an image which comprises a labeled representation of at least some of the plurality of anatomical structures, and an image from which at least one of the plurality of anatomical structures has been omitted.

17. The apparatus according to claim 1, wherein the first anatomical structure or group of anatomical structure is larger than the second anatomical structure or group of anatomical structures.

18. The apparatus according to claim 1, wherein the first group of anatomical structures and the second group of anatomical structures have common members, or the second group is a sub-group of the first group.

19. The apparatus according to claim 1, wherein the reference data set comprises an atlas in which each of the plurality of anatomical structures is individually identified.

20. The image processing apparatus according to claim 1, wherein the volumetric medical imaging data comprises at least one of CT data, MR data, PET data, SPECT data, cone beam CT data, and rotational X-ray data.

21. An imaging data processing method, comprising:
obtaining a hierarchical registration between a reference data set and volumetric medical imaging data, the reference data set comprising a plurality of anatomical structures, wherein the obtaining of the hierarchical registration comprises
selecting, in the reference data set, a first anatomical structure or group of anatomical structures and a second, different anatomical structure or group of anatomical structures, wherein the first anatomical structure or group of anatomical structures is larger and/or more static than the second anatomical structure or group of anatomical structures;
performing a first registration to obtain a first rigid or affine transformation between a first subset of the reference data set comprising the first anatomical structure or group of anatomical structures and at least a first part of the volumetric medical imaging data;
segmenting the first anatomical structure or group of anatomical structures in the volumetric medical imaging data in dependence on the first registration;
performing a second registration to obtain a second rigid or affine transformation between a second subset of the reference data set comprising the second anatomical structure or group of anatomical structures and at least a second part of the volumetric medical imaging data, wherein the second rigid or affine transformation is obtained by refining the first rigid or affine transformation; and
segmenting the second anatomical structure or group of structures in the volumetric medical imaging data in dependence on the second registration, such that the first anatomical structure or group of anatomical structure and the second anatomical structure or group of structures are segmented in the volumetric medical Imaging data using different, successive registrations.

22. A non-transitory computer-readable storage medium storing a computer program comprising computer-readable instructions that are executable to perform a method comprising:
obtaining a hierarchical registration between a reference data set and volumetric medical imaging data, the reference data set comprising a plurality of anatomical structures, wherein the obtaining of the hierarchical registration comprises
selecting, in the reference data set, a first anatomical structure or group of anatomical structures and a second, different anatomical structure or group of anatomical structures, wherein the first anatomical structure or group of anatomical structures is larger and/or more static than the second anatomical structure or group of anatomical structures;
performing a first registration to obtain a first rigid or affine transformation between a first subset of the reference data set comprising the first anatomical structure or group of anatomical structures and at least a first part of the volumetric medical imaging data;
segmenting the first anatomical structure or group of anatomical structures in the volumetric medical imaging data in dependence on the first registration;
performing a second registration to obtain a second rigid or affine transformation between a second subset of the reference data set comprising the second anatomical structure or group of anatomical structures and at least a second part of the volumetric medical imaging data, wherein the second rigid or affine transformation is obtained by refining the first rigid or affine transformation; and
segmenting the second anatomical structure or group of structures in the volumetric medical imaging data in dependence on the second registration, such that the first anatomical structure or group of anatomical structure and the second anatomical structure or group of structures are segmented in the volumetric medical Imaging data using different, successive registrations.

* * * * *